(12) United States Patent
Atiba et al.

(10) Patent No.: US 11,213,532 B2
(45) Date of Patent: *Jan. 4, 2022

(54) THERAPY AND PREVENTION OF PRION PROTEIN COMPLEX INFECTIONS IN NON-HUMAN ANIMALS

(71) Applicants: Joshua O. Atiba, Watsonville, CA (US); Steven C. Sereboff, Santa Barbara, CA (US)

(72) Inventors: Joshua O. Atiba, Watsonville, CA (US); Steven C. Sereboff, Santa Barbara, CA (US)

(*) Notice: Subject to any disclaimer, the term of this patent is extended or adjusted under 35 U.S.C. 154(b) by 28 days.

This patent is subject to a terminal disclaimer.

(21) Appl. No.: 16/921,666

(22) Filed: Jul. 6, 2020

(65) Prior Publication Data
US 2020/0330490 A1    Oct. 22, 2020

Related U.S. Application Data

(60) Continuation of application No. 16/565,242, filed on Sep. 9, 2019, now Pat. No. 10,729,705, which is a
(Continued)

(51) Int. Cl.
*A61K 31/65* (2006.01)
*A61P 33/00* (2006.01)
(Continued)

(52) U.S. Cl.
CPC .......... *A61K 31/65* (2013.01); *A61K 9/0053* (2013.01); *A61P 31/00* (2018.01); *A61P 31/04* (2018.01);
(Continued)

(58) Field of Classification Search
CPC .... A61K 31/415; A61K 31/65; A61K 9/0053; A61K 314/436; A61K 45/06; A61P 33/00; A61P 31/00
See application file for complete search history.

(56) References Cited

U.S. PATENT DOCUMENTS 9,453,079 B2    9/2016   Atwal et al.
9,919,021 B2    3/2018   Ferreira Vila Real et al.
9,999,624 B2    6/2018   May et al.

OTHER PUBLICATIONS

Budni, Josiane & Garcez, Michelle & de Medeiros, J & Cassaro, E & Santos-Bellettini, T & Mina, F & Quevedo, Joao. (2016). The Anti-Inflammatory Role of Minocycline in Alzheimer's Disease. Current Alzheimer research. Bentham Science Publishers, vol. 13, No. 12.
(Continued)

*Primary Examiner* — Savitha M Rao
(74) *Attorney, Agent, or Firm* — Socal IP Law Group LLP; Brian S. Tamsut

(57) ABSTRACT

There are disclosed therapies and preventions of prion protein complex infections. The transcription of the amyloid precursor protein gene and PrP gene and the RNA transcript are the rate-limiting steps and are most susceptible for blockage and control of the process of amyloid protein formation and $PrP^{sc}$ formation. Thus, therapies and prevention regimes for prion protein complex infections interrupt this process at the level of DNA transcription to RNA, RNA transport to the mitochondrion for protein synthesis and deposition in the cerebral cortex neurons.

3 Claims, 5 Drawing Sheets

Related U.S. Application Data division of application No. 16/151,193, filed on Oct. 3, 2018, now Pat. No. 10,406,170.

(60) Provisional application No. 62/690,736, filed on Jun. 27, 2018, provisional application No. 62/691,910, filed on Jun. 29, 2018, provisional application No. 62/714,012, filed on Aug. 2, 2018.

(51) Int. Cl.
    *A61K 9/00*      (2006.01)
    *A61K 31/436*      (2006.01)
    *A61P 31/00*      (2006.01)
    *A61K 45/06*      (2006.01)
    *A61P 37/06*      (2006.01)
    *A61P 31/04*      (2006.01)

(52) U.S. Cl.
    CPC ............... *A61P 33/00* (2018.01); *A61P 37/06* (2018.01); *A61K 9/00* (2013.01); *A61K 31/436* (2013.01); *A61K 45/06* (2013.01); *A61K 2300/00* (2013.01)

(56) References Cited

OTHER PUBLICATIONS

Baskakov et al. Converting the prion protein: What makes the protein infectious, Biochimica et Biophysica Acta (BBA)—Molecular Basis of Disease. vol. 1772, Issue 6, Jun. 2007, pp. 692-703.

Cheng, Shanshan et al. "Minocycline reduces neuroinflammation but does not ameliorate neuron loss in a mouse model of neurodegeneration." Scientific reports (2015).

UK Research and Innovation, Minocycline in Alzheimer's Disease Efficacy Trial: The MADE Trial, Journal, https://gtr.ukri.org/projects?ref=MC_PC_13091. Last accessed Aug. 17, 2018. Total of 4 pages.

Minocycline in Alzheimer's Disease. ISRCTN—ISRCTN06195297: Ongoing 2b/3a Inhibition in Myocardial Infarction Evaluation, www.isrctn.com/ISRCTN16105064. Last accessed Aug. 17, 2018. Total of 7 pages.

Minocycline in Patients With Alzheimer's Disease, NIH U.S. National Library of Medicine, ClinicalTrials.gov, https://clinicaltrials.gov/ct2/show/study/NCT01463384?sect=X4301256. Last accessed Aug. 17, 2018. Total of 16 pages.

Parry T.L., Melehani J.H., Ranek M.J., et al. (May 2015) Functional amyloid signaling via the inflammasome, necrosome, and signalosome: new therapeutic targets in heart failure. Frontiers in Cardiovascular Medicine, vol. 2, Article 25. Total of 14 pages.

Brendan M. Weiss, Sandy W. Wong, Raymond L. Comenzo, Beyond the plasma cell: emerging therapies for immunoglobulin light chain amyloidosis, American Society of Hematology, Journal. Blood May 12, 2016, blood-2015-11-681650; DOI: 10.1182/blood-2015-11-681650. Last accessed Aug. 28, 2018. Total of 7 pages.

Zhou J, Liu B (2013) Alzheimer's disease and prion protein. Intractable & Rare Disease Research, Journal 2(2): pp. 35-44. https://doi.org/10.5582/irdr.2013.v2.2.35. Total of 10 pages.

Dang Pham Kim, Claude Saegerman, Caroline Douny, Ton Vu Dinh, Bo Ha Xuan, Binh Dang Vu, Ngan Pham Hong, Marie-Louise Scippo, First Survey on the Use of Antibiotics in Pig and Poultry Production in the Red River Delta Region of Vietnam, Food and Public Health, vol. 3 No. 5, 2013, pp. 247-256. doi: 10.5923/j.fph.20130305.03.

Min L-J, Kobayashi Y, Mogi M, Tsukuda K, Yamada A, Yamauchi K, et al. (2017) Administration of bovine casein—derived peptide prevents cognitive decline in Alzheimer disease model mice. PLoS ONE 12(2): e0171515. https://doi.org/10.1371/journal.pone.0171515.

Gunn-Moore, Danielle, Oksana Kaidanovich-Beilin, María Carolina Gallego Iradi, Frank Gunn-Moore, and Simon Lovestone. "Alzheimers Disease in Humans and Other Animals: A Consequence of Postreproductive Life Span and Longevity Rather than Aging." Alzheimers & Dementia 14, No. 2 (2018): 195-204. doi:10.1016/j.jalz.2017.08.014.

Parihar, Mordhwaj S., and Gregory J. Brewer. "Amyloid-β as a Modulator of Synaptic Plasticity." Journal of Alzheimers Disease 22, No. 3 (2010): 741-63. doi:10.3233/jad-2010-101020.

Sabate, Raimon, Frederic Rousseau, Joost Schymkowitz, Cristina Batlle, and Salvador Ventura. "Amyloids or Prions? That is the Question." Prion 9, No. 3 (2015): 200-06. doi:10.1080/19336896.2015.1053685.

Thomas, Heather Smith. "Animal Health: Treat Cattle with the Proper Dosage of Antibiotics." Canadian Cattlemen. Sep. 22, 2017. Accessed Sep. 19, 2018. https://www.canadiancattlemen.ca/2017/09/22/animal-health-treat-cattle-with-the-proper-dosage-of-antibiotics/.

Minter, Myles R., Reinhard Hinterleitner, Marlies Meisel, Can Zhang, Vanessa Leone, Xiaoqiong Zhang, Paul Oyler-Castrillo, Xulun Zhang, Mark W. Musch, Xunuo Shen, Bana Jabri, Eugene B. Chang, Rudolph E. Tanzi, and Sangram S. Sisodia. "Antibiotic-induced Perturbations in Microbial Diversity during Post-natal Development Alters Amyloid Pathology in an Aged APPSWE/PS1ΔE9 Murine Model of Alzheimer's Disease." Scientific Reports 7, No. 1 (2017). doi:10.1038/s41598-017-11047-w.

Boyles, Salynn. "Antibiotics May Slow Alzheimer's." WebMD. Oct. 9, 2003. Accessed Sep. 11, 2018. https://www.webmd.com/alzheimers/news/20031009/antibiotics-may-slow-alzheimers#1.

Wood, Matt. "Antibiotics Weaken Signs of Alzheimers in Mice after Just One Week." UChicago Medicine—At The Forefront. Sep. 15, 2017. Accessed Sep. 19, 2018. https://www.uchicagomedicine.org/neurosciences-articles/antibiotics-weaken-signs-of-alzheimers-disease-in-mice-after-just-one-week-of-treatment.

Cheng, Chin, and Valerie Daggett. "Molecular Dynamics Simulations Capture the Misfolding of the Bovine Prion Proteir at Acidic PH." Biomolecules 4, No. 1 (2014): 181-201. doi:10.3390/biom4010181.

Brihoum, M., H. Amory, D. Desmecht, D. Cassart, S. Deleuze, and F. Rollin. "Descriptive Study of 32 Cases of Doxycycline-Overdosed Calves." Journal of Veterinary Internal Medicine 24, No. 5 (2010): 1203-210. doi:10.1111/j.1939-1676.2010.0560.x.

Committee for Veterinary Medicinal Products, Doxycycline Summary Report (2), EMEA/MRL/270/97-FINAL. Available from http://www.ema.europa.eu. 2 pages.

Spires-Jones, Tara L., Melanie Meyer-Luehmann, Jennifer D. Osetek, Phillip B. Jones, Edward A. Stern, Brian J. Bacskai, and Bradley T. Hyman. "Impaired Spine Stability Underlies Plaque-Related Spine Loss in an Alzheimers Disease Mouse Model." The American Journal of Pathology 171, No. 4 (2007): 1304-311. doi:10.2353/ajpath.2007.070055.

Mucke, L., and D. J. Selkoe. "Neurotoxicity of Amyloid—Protein: Synaptic and Network Dysfunction." Cold Spring Harbor Perspectives in Medicine 2, No. 7 (2012). doi: 10.1101/cshperspect.a006338.

L A. Meijer , K. G F. Ceyssens , B. I. J. A. C. de Grève & W. de Bruijn (1993) Pharmacokinetics and bioavailability of doxycycline hyclate after oral administration in calves, Veterinary Quarterly, 15:1, 1-5, DOI: 10.1080/01652176.1993.9694358.

Lee J, Kim SY, Hwang KJ, Ju YR, Woo H-J. Prion Diseases as Transmissible Zoonotic Diseases. Osong Public Health and Research Perspectives. 2013;4(1):57-66. doi:10.1016/j.phrp.2012.12.008.

Newport, Alan. "Remote Drug Delivery Passes the Test." Beef Producer. Aug. 15, 2018. Accessed Sep. 19, 2018. https://www.beefproducer.com/antibiotics/remote-drug-delivery-passes-test.

Dvorsky, George. "Signs of Alzheimer's Detected in Brains of Chimps For First Time." Gizmodo. Aug. 1, 2017. Accessed Sep. 19, 2018. https://gizmodo.com/signs-of-alzheimer-s-detected-in-brains-of-chimps-for-f-1797433524.

Thomson Micromedex "Tetracyclines Veterinary—Systemic". 2003, 51 pages. Accessed Sep. 19, 2018. https://cdn.ymaws.com/www.aavpt.org/resource/resmgr/imported/tetracyclines.pdf.

Simon, Sharon Lr, Lise Lamoureux, Margot Plews, Micheal Stobart, Jillian Lemaistre, Ute Ziegler, Catherine Graham, Stefanie Czub, Martin Groschup, and J. David Knox. "The Identification of Disease-

(56) References Cited

OTHER PUBLICATIONS induced Biomarkers in the Urine of BSE Infected Cattle." Proteome Science 6, No. 1 (2008): 23. doi:10.1186/1477-5956-6-23.
Dvorsky, George. "Traces of Alzheimer's Disease Detected in Wild Animals for the First Time." Gizmodo. Oct. 23, 2017. Accessed Sep. 19, 2018. https://gizmodo.com/traces-of-alzheimer-s-disease-detected-in-wild-animal-f-1819769344.
"Antibiotic Treatment Weakens Progression of Alzheimer's Disease through Changes in the Gut Microbiome." UChicago Medicine. Accessed Sep. 11, 2018. http://www.uchospitals.edu/news/2016/20160721-alzheimers.html.
Bousfield, Barry, Brown, Richard. Veterinary Drugs: Veterinary Bulletin—Agriculture, Fisheries and Conservation Department Newsletter. (Kong Kong) vol. 1, Issue No. 9, Jul. 2012. 16 pages.
Veterinary Drug Formulary—English Language Edition 2014. Formulary of the CSU VTH, Plumb.Accessed Sep. 19, 2018. https://www.cvmbs.colostate.edu/aphi/web/outreach/. 19 pages.
Heerema, Esther, and Claudia Chaves. "Why Families Might Decide Not to Give Antibiotics in Late-Stage Dementia." Verywell Health. Accessed Sep. 19, 2018. https://www.verywellhealth.com/antibiotic-use-in-advanced-dementia-98209.
Lachance, Daniel H., Vanda A. Lennon, Sean J. Pittock, Jennifer A. Tracy, Karl N. Krecke, Kimberly K. Amrami, Eric M. Poeschla, Robert Orenstein, Bernd W. Scheithauer, James J. Sejvar, Stacy Holzbauer, Aaron S. Devries, and P. James B Dyck. "An Outbreak of Neurological Autoimmunity with Polyradiculoneuropathy in Workers Exposed to Aerosolised Porcine Neural Tissue: A Descriptive Study." The Lancet Neurology 9, No. 1 (2010): 55-66. doi:10.1016/s1474-4422(09)70296-0.
Per Hammarström & Sofie Nystrom (2015) Porcine prion protein amyloid, Prion, 9:4, 266-277, DOI:10.1080/19336896.2015.1065373.
Wells, G. A. H. "Studies of the Transmissibility of the Agent of Bovine Spongiform Encephalopathy to Pigs." Journal of General Virology 84, No. 4 (2003): 1021-031. doi:10.1099/vir.0.18788-0.
Bleifuss, Joe. "Mad Cow Disease" From Pork May Cause Some Alzheimer's. (May 27, 1997) Albion Monitor. Accessed Sep. 23, 2018. http://albionmonitor.com/9706a/madpig.html.
Dr Theo A. Niewold, Charles L. Murphy, Mathilda J. M. Toussaint, Alan Solomon & Erik Gruys (2005) Chemical typing of porcine systemic amyloid as AA-amyloid, Amyloid, 12:3, 164-166, DOI: 10.1080/13506120500231806.
Fernández-Borges N, Chianini F, Eraña H, et al. Naturally prion resistant mammals: A utopia? Prion. 2012;6(5):425-429. doi: 10.4161/pri.22057.
Wehrfritz, George. "Now, 'Mad Pig' Disease." Newsweek. Mar. 13, 2010. Accessed Sep. 23, 2018. https://www.newsweek.com/now-mad-pig-disease-171658.
Hedman C, Bolea R, Marín B, et al. Transmission of sheep-bovine spongiform encephalopathy to pigs. Veterinary Research. 2016;47:14. doi:10.1186/s13567-015-0295-8.
Lu Z, Liu F, Chen L, Zhang H, Ding Y, Liu J, et al. (2015) Effect of Chronic Administration of Low Dose Rapamycin on Development and Immunity in Young Rats. PLoS ONE 10(8): e0135256. doi:10.1371/journal.pone.0135256.
Curtis, Richelle L. "Mammary mTOR Activity during Intravenous Glucose Infusions into Lactating Dairy Cows" Jul. 2013. University of Guelph. 58 pages.

Miller, Richard A.; Harrison, David E.; Astle, Clinton M.; Fernandez, Elizabeth; Flurkey, Kevin; Han, Melissa; Javors, Martin A.; Li, Xinna; Nadon, Nancy L.; Nelson, James F.; Pletcher, Scott; Salmon, Adam B.; Sharp, Zelton Dave; Van Roekel, Sabrina; Winkleman, Lynn; Strong, Randy (2014). "Rapamycinmediated lifespan increase in mice is dose and sex dependent and metabolically distinct from dietary restriction." Aging Cell 13(3): 468-477.
"APSALIQ DOXYCYCLINE 200", Andres Pintaluba, S.A.(Spain). 2 pages.
"Coloxan Oral." Interchemie Werken. Accessed Sep. 28, 2018. https://www.interchemie.com/veterinary-medicines/coloxan-oral.html.
"Neoral, Sandimmune (cyclosporine) Dosing, Indications, Interactions, Adverse Effects and More." Medscape Drugs & Diseases—Page Not Found. Dec. 30, 2016. Accessed Sep. 28, 2018. https://reference.medscape.com/drug/neoral-sandimmune-cyclosporine-343196.
D Spriggs, J Griffin, J Wisch and D Kufe. "Clinical pharmacology of low-dose cytosine arabinoside" Blood Journal. 1985 65: 1087-1089. 4 pages.
Yeruham I, Perl S, Sharony D, Vishinisky Y: Doxycycline toxicity in calves in two feedlots. J Vet Med Ser B. 2002, 49: 406-408. 10.1046/j.1439-0450.2002.00597.x.
El-Neweshy MS. Experimental doxycycline overdose in rats causes cardiomyopathy. International Journal of Experimental Pathology. 2013;94(2):109-114. doi:10.1111/iep.12013.
"Calculations and Conversions for Drugs, Forage, Feed and Water Consumptions". FARAD Unit Conversion Document. Food Animal Residue Avoidance & Depletion Species Pages. Jan. 2016. 12 pages.
Siegmund, Stephanie E., Hua Yang, Rohit Sharma, Martin Javors, Owen Skinner, Vamsi Mootha, Michio Hirano, and Eric A. Schon. "Low-dose Rapamycin Extends Lifespan in a Mouse Model of MtDNA Depletion Syndrome." Human Molecular Genetics 26, No. 23 (2017): 4588-605. doi:10.1093/hmg/ddx341.
Pfizer "Doxycycline hyclate capsules—Material Safety Data Sheet". Revision Date Jan. 2, 2007, version 2.5. 6 pages.
Zhang, JiaWei, Fan Zhao, and Qing Sun. "Metformin Synergizes with Rapamycin to Inhibit the Growth of Pancreatic Cancer In vitro and In vivo." Oncology Letters, 2017. doi:10.3892/ol.2017.7444.
"Minocycline for Veterinary Use." Wedgewood Pharmacy. Accessed Sep. 25, 2018. https://www.wedgewoodpetrx.com/learning-center/professional-monographs/minocycline-for-veterinary-use.html.
Maaland, Marit G., Luca Guardabassi, and Mark G. Papich. "Minocycline Pharmacokinetics and Pharmacodynamics in Dogs: Dosage Recommendations for Treatment of Meticillin-resistant *Staphylococcus pseudintermedius* Infections." Veterinary Dermatology 25, No. 3 (2014). doi:10.1111/vde.12130.
Zhang, Bodi. Current Neurology and Neuroscience Reports. 2009. Accessed Sep. 28, 2018. https://www.ncbi.nlm.nih.gov/pmc/articles/PMC2726602/.
"Plumb's Veterinary Drug Handbook 6th Edition PDF." Veterinary Discussions. Feb. 7, 2018. Accessed Sep. 25, 2018. https://www.veterinarydiscussions.net/plumbs-veterinary-drug-handbook-6th-edition-pdf/.
Guba, Markus, Gudrun E. Koehl, Evelyn Neppl, Axel Doenecke, Markus Steinbauer, Hans J. Schlitt, Karl-Walter Jauch, and Edward K. Geissler. "Dosing of Rapamycin Is Critical to Achieve an Optimal Antiangiogenic Effect against Cancer." Transplant International 18, No. 1 (2005): 89-94. doi:10.1111/j.1432-2277.2004.00026.x.
Ellebrecht, Christoph T. "Subcutaneous Veltuzumab in Refractory Pemphigus." JAMA. Dec. 1, 2014. Accessed Sep. 28, 2018. https://jamanetwork.com/journals/jamadermatology/fullarticle/1896522.

The Witch's Brew

THERAPY AND PREVENTION OF PRION PROTEIN COMPLEX INFECTIONS IN NON-HUMAN ANIMALS

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by anyone of the patent disclosure as it appears in the Patent and Trademark Office patent files or records, but otherwise reserves all copyright and trade dress rights whatsoever.

RELATED APPLICATION INFORMATION

This application is a continuation of application Ser. No. 16/565,242 entitled "Therapy and Prevention of Prion Protein Complex Infections in Non-Human Animals" which is a division of application Ser. No. 16/151,193 entitled "Therapy and Prevention of Prion Protein Complex Infections in Non-Human Animals," now U.S. Pat. No. 10,406,170 B1, which claims priority from the following provisional patent applications: Application No. 62/690,736 filed Jun. 27, 2018 entitled "Treatment of Alzheimer's Disease;" Application No. 62/691,910 filed Jun. 29, 2018 entitled "Preventive Therapy of Alzheimer's Disease;" and Application No. 62/714,012 filed Aug. 2, 2018 entitled "Therapy and Prevention of Alzheimer's Disease."

BACKGROUND

Field

This disclosure relates to therapy and prevention of prion protein complex infections.

Description of the Related Art

Neurodegenerative diseases and prion protein complex infections affect both humans and other mammals. The wide variety of these diseases has led to a wide variety of views of their causes, and generally each is believed to have a different cause.

In humans, Alzheimer's disease (AD) is commonly believed to be a localized brain disease. AD with neurological disease is the third leading cause of death in humans in the United States after cardiovascular diseases and cancer. AD normally follows a sequence comprised of neuroinflammation, amyloid and tau proteopathy, accumulative storage disease, neurotoxicity and neuron damage, loss of function (i.e., activities of daily living (ADL) and cognitive skills), and finally death. AD deaths are due to the futility and loss of will to live in these patients who have been depersonalized and lost the will to live, coupled with the failure to thrive leading to premature death usually within five to ten years of diagnosis of AD.

AD and dementia were long thought to only affect human beings. However recent research suggests that the longer an organism with neural tissue lives, the more susceptible it may be to developing AD or similar diseases. For example, some researchers report that primates, dogs, cats, dolphins, and sea lions exhibit AD.

There are four main prevailing theories about the causation of AD: (a) a cholinergic hypothesis, (b) an amyloid protein deposition hypothesis, (c) a tau protein deposition hypothesis, and (d) a neurovascular hypothesis. Presently there is no effective treatment capable of modifying the progression of Alzheimer's disease, or preventing its onset. Currently available therapies only act on symptomatic improvement, while the development of therapies capable of blocking or delaying the disease progression remains a challenging unmet need.

According to the cholinergic hypothesis, degeneration of cholinergic neurons in the basal forebrain and the associated loss of cholinergic neurotransmission in the cerebral cortex and other areas contribute significantly to the deterioration in cognitive function seen in patients with Alzheimer's disease.

Under the amyloid protein deposition hypothesis, the formation of amyloid plaques and neurofibrillary tangles are thought to contribute to the degradation of the neurons (nerve cells) in the brain and the subsequent symptoms of Alzheimer's disease. Amyloid proteins are a large group of proteins of which sixty different types have been described. Thirty-six amyloid proteins have been associated with human disease. Amyloid protein defects have also been linked to AD-like diseases in cows, primates, dolphins, cats, and minks. Amyloid protein was first seen and described by Rudolf Virchow who thought it was a starchy substance hence the name amyloid related to starch or "amylin" in Latin. It was next thought to be a fatty substance, but later found to be a protein substance. Since the introduction of elegant protein chemistry, mass spectrometry, and x-ray crystallography, amyloid proteins have been sequenced, observed, better characterized, and classified in various mammalian diseases and conditions.

Amyloid protein disease was once classified as a primary or secondary disease. Primary disease was recognized as synthesis and deposition of the protein in organs such as the heart, kidney, skin, tongue etc. In secondary disease, amyloid protein deposition was recognized as secondary to a chronic suppurative condition such as tuberculosis or other uncontrolled bacterial abscess which is common in developing nations of the world. Similarly, chronic inflammatory conditions, such as rheumatoid arthritis and renal dialysis, lead to reactive amyloid protein deposition.

Amyloid precursor protein (APP), which is encoded in chromosome 21 of humans, has a role in AD. APP is a trans-membrane protein that penetrates through the neuron's membrane, and is critical for neuron growth, survival, and post-injury repair. Thus, loss of a neuron's APP may lead to physiological deficits that contribute to dementia. Clinical data from humans with Down syndrome (i.e., trisomy 21) shows that they develop AD earlier in their 40s, since the gene for APP is in chromosome 21, and they are saddled with three copies. This is akin to patients with inflammatory bowel disease (IBD) who develop colon cancer in their 30s-40s compared to the normal population that develops it in their 50s-80s. APP is copied and used to synthesize amyloid protein.

Amyloid beta (AB) is the specific amyloid protein implicated in AD. Amyloid plaques are made up of small peptides, 39-43 amino acids in length. Amyloid beta is produced from the sequential cleavage of APP by beta-site amyloid precursor protein-cleaving enzyme 1 (BACE-1) followed by gamma-secretase. In AD, gamma secretase and beta secretase act together in a proteolysis catabolic reaction, cleaving a smaller fragment of APP. These protein catabolism fragments then form fibrils of amyloid beta, which further form clumps deposited outside the neurons known as senile plaques.

Because AB accumulates excessively in AD, there is a logical inference that its precursor, APP, would be elevated as well. However, a study has shown that neuronal cell bodies contain less APP as a function of their proximity to amyloid plaques. It has been theorized that this APP deficit near AB plaques results from a decline in production of APP which normally rises in response to stress.

Several BACE-1 inhibitors and humanized monoclonal antibodies to soluble amyloid protein have been in clinical trials as a treatment for AD. These trials failed to deliver on the promise of being disease modifying drug (DMD) agents (i.e., they change the underlying pathology of the disease) in AD. Similarly, vaccines have been tried to clear amyloid protein plaques in AD all to no avail. In light of the failure of clinical trials using BACE inhibitors, and the failure of amyloid immunotherapy with intravenous Solanezumab, the amyloid protein deposition theory has been called into question.

The tau protein deposition hypothesis proposes that tau protein abnormalities initiate the disease cascade. In this model, hyperphosphorylated tau begins to pair with other threads of tau. Eventually, they form neurofibrillary tangles inside nerve cell bodies. When this occurs, the microtubules disintegrate, destroying the structure of the cell's cytoskeleton which collapses the neuron's transport system. Other studies in mammals especially in mice confirm that when tau is hyperphosphorylated, the animal suffers from cognitive impairments. This may result first in malfunctions in biochemical communication between neurons and later in the death of the cells.

The neurovascular hypothesis claims that a substantial amount of AB peptides in the brain of Alzheimer's disease patients originates in the systemic circulation. According to this theory, poor functioning of the blood-brain barrier (BBB) is involved. One side effect of this poor function is production of amyloid and tau hyperphosphorylation.

Prion (PrP) is a protein which arises from misfolding of a normal protein. The two forms of prion are designated as $PrP^c$, which is a normally folded protein, and $PrP^{sc}$, a misfolded form which gives rise to the disease. Normal PrP is believed to be harmless and expressed ubiquitously in all mammalian cells. The two forms do not differ in their amino acid sequence, however the pathogenic $PrP^{sc}$ isoform differs from the normal $PrP^c$ form in its secondary and tertiary structure. The $PrP^{sc}$ isoform is more enriched in beta sheets, while the normal $PrP^c$ form is enriched in alpha helices. The differences in conformation allow $PrP^{sc}$ to aggregate and be extremely resistant to protein degradation by enzymes or by other chemical and physical means. The normal form, on the other hand, is susceptible to complete proteolysis and soluble in non-denaturing detergents. It has been suggested that pre-existing or acquired $PrP^{sc}$ can promote the conversion of $PrP^c$ into $PrP^{sc}$, which goes on to convert other $PrP^c$. This initiates a chain reaction that allows for $PrP^{sc}$'s rapid propagation, resulting in the pathogenesis of prion diseases. $PrP^c$ protein is one of several cellular receptors of soluble amyloid beta (Aβ) oligomers.

Against this background of prion protein complex infections, we turn to several drugs which have not been proposed for therapeutic application toward prion protein complex infections. For example, although genetically engineered antibodies have been tried, antibiotics have not been exclusively considered or taken seriously as possible therapies for prion protein complex infections. Another class not previously considered are immunosuppressants.

The tetracyclines are a very old group of bacteriostatic antibiotics consisting of tetracycline, doxycycline, and minocycline. They act by inhibiting protein synthesis in bacterial and protozoa cells and in eukaryotic mitochondria, inhibiting the binding of aminoacyl-tRNA to the mRNA ribosome complex. They do so mainly by binding to the 30S ribosomal subunit in the mRNA translation complex. In addition to inhibiting protein synthesis, these drugs are anti-inflammatory, are lipid soluble, and have a high central nervous system concentration. Tetracyclines have been used in animal husbandry to fight certain infections in cattle, as well as veterinary medicine for years.

Sirolimus, also known as rapamycin, is a macrolide compound marketed under the trade name Rapamune by Pfizer. Sirolimus has immunosuppressant effects in humans and is used in preventing the rejection of kidney transplants. It inhibits activation of T cells and B cells by reducing their sensitivity to interleukin-2 (IL-2) through mTOR inhibition. By its effect on B cells it prevents the humoral immune system from synthesizing humoral antibodies to the renal graft.

Perhaps the most infamous nonhuman mammalian neurological prion disease is bovine spongiform encephalopathy (BSE) or "Mad Cow Disease." Other prion diseases include scrapie (affecting both sheep and goats), transmissible mink encephalopathy (affecting minks), chronic wasting disease (CWD) (affecting elk and deer), feline spongiform encephalopathy (FSE) (affecting cats), and exotic ungulate encephalopathy (EUE) (affecting exotic mammals from Africa such as nyala and greater kudu).

The usual approach to nonhuman mammalian neurological prion disease is oriented to the herd. The typical approach when an infected individual is identified is to kill the entire herd and carefully dispose of the carcasses.

DETAILED DESCRIPTION

Figure 1:
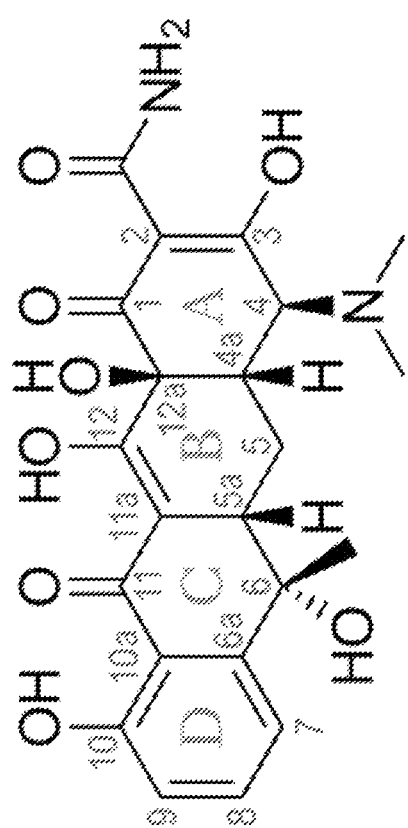
FIG. 1 is a skeletal formula of tetracycline with atoms and four rings numbered and labeled.
Figure 2:
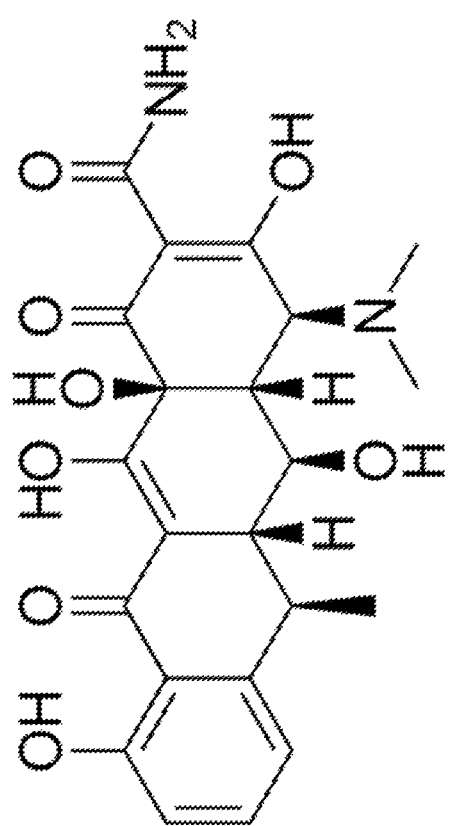
FIG. 2 is a formula for doxycycline.
Figure 3:
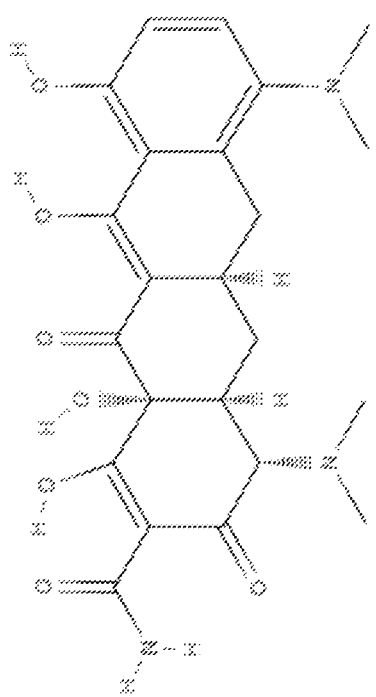
FIG. 3 is a formula for minocycline.
Figure 4:
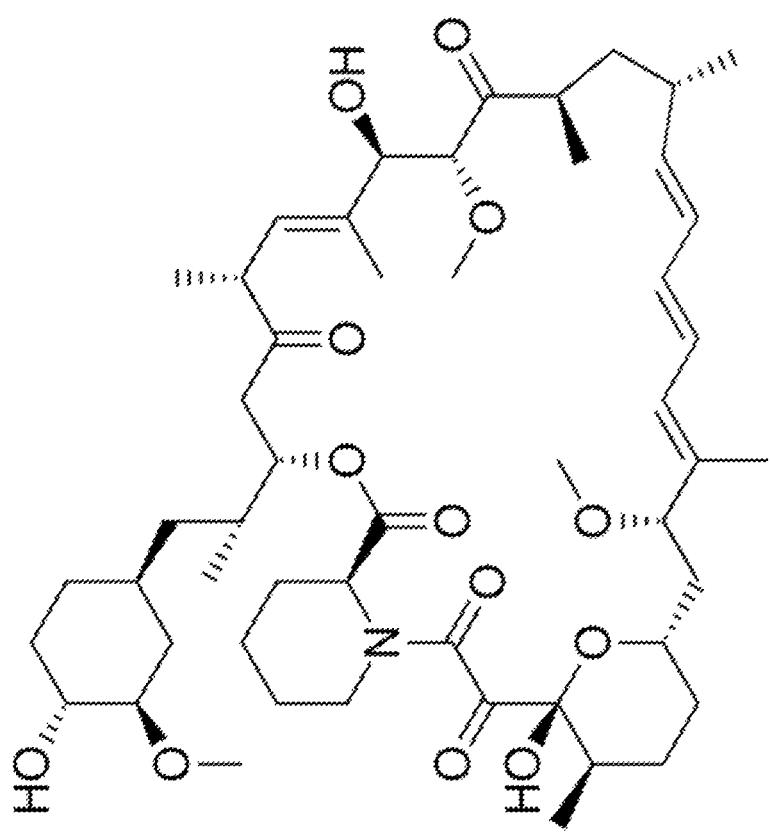
FIG. 4 is a formula for sirolimus.
Figure 5:
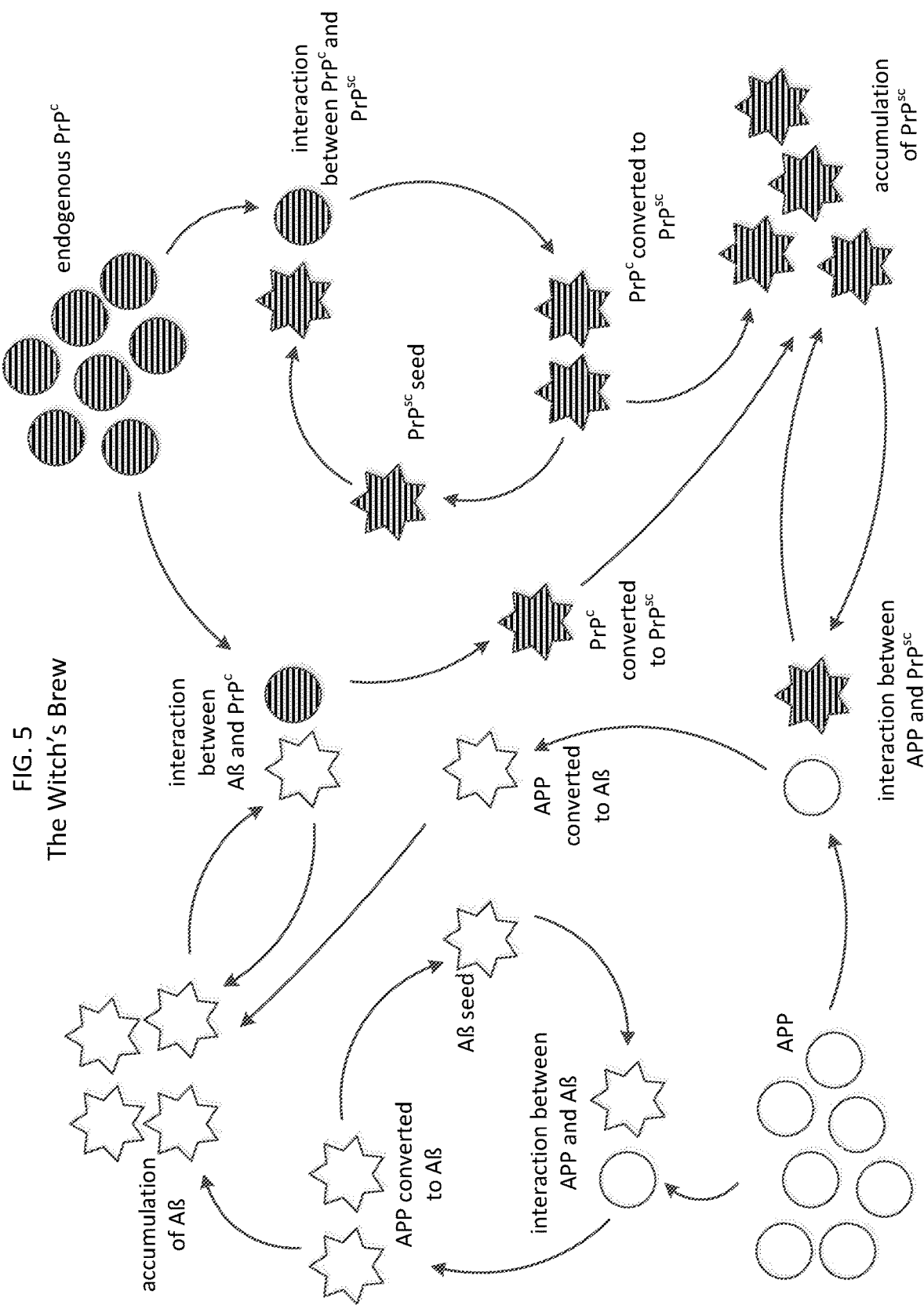
FIG. 5 is a conceptual diagram showing how the basis for exponential growth of the presence of Aβ and $PrP^{sc}$.

AD is not a localized brain disease. Like other prion protein complex infections, AD is a systemic disease involving the body, the peripheral circulation, and B-cells. Misfolded proteins and neural plaque are found in the brain, spinal cord and neurons throughout the body. AD includes a localized reaction in the neocortex. Indeed, proof of this is the fact that AD can be diagnosed in saliva by testing for Ab42 level (with ELISA test), blood Ab42/40 ratio, and cerebrospinal Ab42 level.

Amyloid beta protein deposition seen in neurodegenerative diseases is secondary to a chronic neuro-inflammatory condition in the acetylcholine discharging neurons of the cerebral cortex. In humans, this amyloid protein deposition starts ten to fifteen years prior to the clinical diagnosis of AD in the patient and continues until the patient dies. In animals such as cattle the process can be much quicker. Misfolded proteins can accumulate in the brain and take only a few months before symptoms begin to show. As a general rule, the older an animal becomes, the more likely it is to show symptoms of a neurodegenerative disease. The transcription of the APP gene and the RNA transcript are the rate-limiting steps and are most susceptible for blockage and control of the process of amyloid protein formation. Thus, there is described herein a cure for mammalian prion protein complex infections and other neurodegenerative diseases based upon interruption of this process at the level of DNA transcription to RNA, RNA transport to the mitochondrion for protein synthesis and deposition in the cerebral cortex neurons. This is the main thrust of our effort in introducing the first DMDs in prion protein complex infections.

This neuroinflammation in the neocortex is concomitant with localized secretion of amyloid beta to the acetylcholine secreting memory nerve fibers, and the secretion of cellular prion protein ($PrP^c$) peptides and tau protein peptides. The neurotoxicity of the amyloid protein oligomers causes misfolding of the $PrP^c$ peptides, converting the healthy alpha helical rich structures to beta helical rich structures (i.e. $PrP^{sc}$). The $PrP^{sc}$ beta helical structure interacts with AB fibrils and starts laying down sheets of AB fibrils which are neurotoxic and adversely affect nerve fiber, often causing nerve cell death which creates the pathognomonic amyloid plaques and tau protein tangles.

The preventative and curative therapies described herein for prion protein complex infections have a dual interaction. This dual interaction is necessary to halt the progress of the disease, undo at least some neurological damage, and prevent damage from re-arising or recurring. FIG. 5 demonstrates the basis for exponential growth of the presence of Aβ and $PrP^{sc}$. As shown in FIG. 5, when $PrP^{sc}$ is applied to $PrP^c$, the $PrP^c$ misfolds into $PrP^{sc}$. The same behavior arises with APP and Aβ:Aβ is a seed for producing more AB from APP. However, these two cycles are not independent. They are interdependent. That is, AB seeds cause conversion of $PrP^c$ into $PrP^{sc}$, and $PrP^{sc}$ seeds production of AB from APP. Thus, this "witch's brew" of Aβ and $PrP^{sc}$ is at the heart of prion protein complex infections and is a cycle of death which cannot be stopped by a therapy which only interferes with misfolding of $PrP^c$ into $PrP^{sc}$, or only interferes with production of Aβ from APP. The therapy described herein addresses both types of misfolding.

Prion protein complex infections may be treated and prevented through two treatment forms. In these infections, amyloid beta protein, present in the blood, diffuses into the cerebrospinal fluid which washes over the brain and the neocortex. This creates a secondary neocortical reaction with the laying of protein sheets and sheets of amyloid beta fibrils, leading to the death and destruction of memory cells and creating amyloid plaques and neurofibrillary tau protein tangles. One treatment form uses an immunosuppressant to address the systemic humoral B cell reaction and prion protein transcription, translation, and synthesis. The other treatment form uses an antibiotic to address synthesis of amyloid beta protein. Benefits are obtained by combining the treatment forms.

Prion protein complex infections arise from a complex of rogue prion proteins—a witch's brew. This rogue prion protein complex consists of AB fibrils and prion protein beta ($PrP^{sc}$) fibrils. The body's natural reaction to the rogue prion protein complex is a self-defense mechanism that itself irreparably destroys tissue. These defense mechanisms take the form of a self-assembling Pacman (Pcm) protein which attacks and eats the rogue prion protein complex. Injury to the corresponding tissue is the culprit in the pathogenesis of AD and other prion protein complex infection diseases.

The systemic disease component of prion protein complex diseases may be treated with an immunosuppressant such as sirolimus. Sirolimus, by its effect on B cells, impairs the humoral immune system from synthesizing humoral antibodies and APP. This abrogates the systemic component of the AD pathogenesis. Sirolimus can be given to animals in a dosage of either 0.2 mg-3 mg or 0.2 mg-3 mg/kg of animal weight.

The central nervous system (CNS) localized effects of prion protein complex infections may be treated with antibiotics such as tetracyclines. Tetracyclines block protein synthesis by their effects on transcription, translation, and binding to ribosomal protein complexes. Thetetracycline compounds can deal with the CNS/neocortical component of the AD pathogenesis by inhibiting the transcription of the APP gene on chromosome 21 and the transcription of the PrP gene on chromosome 20. Additionally, the tetracyclines block translation of the gene and protein synthesis by binding to the 30S and 50S subunits of ribosomal protein complexes.

The double action through treatment of both the systemic disease component and the CNS localized effects leads to hindering or abolition of the effect of the rogue prion protein complex. By inhibiting the transcription and blocking the synthesis of amyloid protein in mammals afflicted with neurodegenerative disorders, we stop further amyloid protein deposition in the cerebral cortex and the subsequent neurotoxicity and neuronal damage and loss of memory and function. Animals accordingly regain function and have normal healthy neurological function. Similarly, by blocking the transcription and synthesis of $PrP^{sc}$, the second part of the rogue prion protein complex is disrupted.

For animals with neurodegenerative disorders, the therapy may be either an antibiotic alone, or an antibiotic in combination with an immunosuppressant. The appropriate dosage of antibiotic may change based on what type of animal and what type of administration (e.g., antibiotic by injection, feed, water, etc.) is used to administer the treatment. For an adult human, an appropriate therapy may be one of the following: (a) doxycycline 100 mg twice per day such as in the morning and in the evening; (b) a first dose of doxycycline 100 mg and sirolimus 2 mg taken together, such as in the morning, and a separate dose of doxycycline 100 mg at another time, such as in the evening; (c) minocycline 100 mg and sirolimus 2 mg taken at the same time such as in the morning; (d) a single dose of minocycline 100 mg, such as in the morning.

The treatment may be administered in a number of ways depending on the animal as well as how the animal is raised. Dosages of tetracycline and immunosuppressant may be specified as milligrams of drug per kilogram or pound of animal weight. Immunosuppressants are not commonly administered to non-human animals but may need to be for the treatment to be effective. Animals fighting a prion protein infection may need to be kept on antibiotics for a long period (e.g., two weeks to three months) to fight prion infections. Additionally, in certain situations it may be impractical to give a specific dosage to each animal in a herd. A caretaker may want to focus on supplementing an animal's feed or water with enough drug so that the drug remains biologically active enough to combat prion protein complex infections, but not overdose and harm the animal.

The term herd means an assembly of five or more animals of the same species which are in close physical relation to one another for a period of at least one week. With respect to livestock, the animals in the herd live or feed together. With respect to a herd of wild animals, the animals live together within the same vicinity such that they are within eyesight of one another on a day-to-day basis. The animals in a herd may self-assemble or may be assembled by one or more humans. A given animal may be a member of plural herds. One herd may be a subset of another herd, and two herds may have overlapping members.

The term caretaker means a person responsible for an animal's medication, shelter or food. A caretaker may be, for example, an animal's owner, a veterinarian, a veterinarian's agent or assistant, a groomer or a farmhand.

For cows, one treatment may be directed to calves. An appropriate time for an antibiotic regiment to start is after the calves have been weaned from their mother and are at least 200 lbs. In the US, there is typically a waiting period of two to three months after antibiotics have been administered to cattle before they can be slaughtered for food. Administering the antibiotic in this window is favorable because administration of the treatment will not delay slaughter, while ensuring the meat is not contaminated. It also allows treatment at a relatively low weight, thus reducing the amount of drugs administered.

For a calf weaned from its mother an appropriate treatment may be (a) doxycycline 10 mg/kg of weight twice per day such as in the morning and in the evening; (b) a first dose of doxycycline 10 mg/kg and sirolimus 2 mg/kg taken together, such as in the morning, and a separate dose of doxycycline 10 mg/kg at another time, such as in the evening; (c) minocycline 10 mg/kg and sirolimus 2 mg/kg taken at the same time such as in the morning; (d) a single dose of minocycline 10 mg/kg, such as in the morning. The drugs can be added to the calf's food, water, or milk as discussed more below. Sirolimus may be administered in a single dose not based on the animal's weight, such as a 5 mg or 10 mg tablet, while the antibiotic is still administered based in part on the animal's weight. In certain situations, it may be appropriate to give calves a double dose of treatment. Doubling the dosage may bring about faster results without injury to the young calves.

Swine may also be treated for prion protein complex infections. Swine may take tetracyclines in a dosage of 10 mg/kg. Swine may require a range closer to 50 mg tetracycline/kg of body weight tetracycline for effective treatment. In the case of immunosuppressants, a pig may require 5 mg/day. For swine, a dosage sufficient to give a blood concentration of 1-55 ng sirolimus/mL of blood would also be an appropriate dosage.

For a pig the appropriate treatment may be one of the following (a) doxycycline 50 mg/kg of animal weight twice per day such as in the morning and in the evening; (b) a first dose of doxycycline 50 mg/kg and sirolimus 10 mg/kg animal weight taken together, such as in the morning, and a separate dose of doxycycline 50 mg/kg at another time, such as in the evening; (c) minocycline 50 mg/kg and sirolimus 1 mg/kg taken at the same time such as in the morning; (d) a single dose of minocycline 50 mg/kg, such as in the morning. (e) A dose of doxycycline 10 mg/kg or a dose of minocycline 10 mg/kg.

In sheep and goats, a dosage of tetracycline sufficient to get a concentration of tetracycline in the blood to be 0.008 μg/mL-0.12 μg/mL may be sufficient. 20 mg tetracycline/kg of weight would likely yield this concentration. A treatment of Doxycycline intramuscularly at a dosage of 2 mg/kg may also work. 10 mg/kg of doxycycline by pill or tablet may also work. 11.5 mg/kg doxycycline hyclate if administered through drinking water would also work. If administered through IV A dog may be administered a tetracycline amount of 10 mg/kg of weight, while cats may only need 5-7.5 mg/kg of weight. Minocycline in cats and dogs can be administered in a range of 5-25 mg/kg.

In certain scenarios, it may be impracticable for caretakers to carefully measure out and administer treatments to animals one by one. For example, during the Mad Cow disease scare of 2003, it would be impracticable for ranchers to test each animal on a ranch, determine which ones showed signs of infection, administer a treatment individually to the suspected animals, then monitor the recovery of the animal. In such scenarios it would be appropriate for caretakers to treat the entire herd. In such a case a slight overdose or underdose of animals in the herd would be acceptable. An example of such a therapy could entail: (a) doxycycline either mixed in with and/or suspended in a herd's drinking water for one day, (b) doxycycline and sirolimus either mixed in with and/or suspended in a herd's drinking water the next day, (c) minocycline and sirolimus mixed in with and/or suspended in a herd's drinking water for one meal during the next day, and (d) minocycline mixed in with and/or suspended in a herd's drinking water for one meal the last day. An appropriate dosage would be 100 to 200 grams of tetracycline per ton of animal feed. Immunosuppressants could still be delivered to the animals through other means or added to food at a rate of 10-50 g immunosuppressant per ton of feed. A similar calculation would suffice for water or other drinking liquid, 100 to 200 grams of tetracycline per 1,000 liters of water and 10-50 g immunosuppressant per 1,000 liters of water. The animals may need to keep eating or drinking these treatments for three weeks to three months for the treatment to work properly. Additionally, only one step in the sequence could be selected and perpetuated for three weeks to three months. If a caretaker wanted to be more precise they could use the formula: dose required (mg active/Kg bodyweight/day)×average bodyweight of animal in the herd×number of animals in the herd.

Immunosuppressants that act against B cell activity may be an appropriate substitute for sirolimus. Such immunosuppressants include cyclosporin (1-15 mg/kg), tacrolimus, everolimus, cytosine arabinoside, cyclophosphamide, rituximab, ocrelizumab, ofatumumab, and veltuzumab. An immunosuppressant that acts on all the cells of the immune system (including B cells) may be suitable.

For cyclosporin a dose within the range of 1-15 mg/kg may be acceptable. For tacrolimus a dosage of 0.01 mg/kg-0.15 mg/kg is acceptable. For everolimus a dosage in the range of 0.5 mg-3 mg or 0.5 mg/kg-3 mg/kg is acceptable. Cytosine arabinoside is usually deliver based on a dosage of body surface area (BSA) rather than mg/kg. A dosage of 10-20 mg/m$^2$ is acceptable. For cyclophosphamide a dosage in the range of 1-50 mg/kg is acceptable. If using BSA 400-1800 mg/m$^2$ is also acceptable. For rituximab a dosage of 375 mg/m$^2$ is acceptable. For ocrelizumab an injection of 30 mg/mL of 10 mL of solution is acceptable in an adult human. For ofatumumab 285 mg-300 mg for an adult human is acceptable. For veltuzumab BSA may be used and a dosage of 188 mg/m$^2$ for a human is acceptable.

After a few days or weeks of treatment, animals may begin to regain normal function and cease to exhibit symptoms of prion protein complex infections. It may be appropriate to continue treatment nonetheless, for example because they may still carry misfolded proteins or seed molecules that need to be cleared out by the rest of the treatment.

Additionally, intravenous (IV) administration of antibiotics and immunosuppressants may be used on animals. When IV is used for animals the dosage can either remain the same or be lessened slightly because treatment bypasses an animal's digestive system. For example, in cows rather than treat them with 10 mg tetracycline/kg of body weight, the dosage may be adjusted down to 7.5 mg tetracycline/kg of body weight when the tetracycline is administered through an IV. A slight overdose of antibiotics is permissible, however to avoid adverse side effects caused by the antibiotics themselves (e.g., drowsiness, trouble walking, inflamed joints, diarrhea) the dosage when administered through IV should be lessened.

A caretaker may find it favorable to administer a tetracycline in a dosage of at least 1 mg per day. A once daily-dosage may be targeted to give a steady state blood level of tetracycline in the range of 0.01 µg/ml and a maximum of 10.0 µg/ml A dose may take the form of a unit dose. That is, a unit dose is a pill, a tablet or a capsule, an injection, a unit of feed, or one unit of a water-based solution—one and only one.

Effectiveness of this therapy is apparent in one to twelve weeks. Once treatment is effective, the animal may discontinue the therapy under controlled observation for relapse and possible retreatment. A test of the animal may indicate the amount of prions or AB, and this may be used beneficially for the treatment regimen.

These therapies may be varied in a number of ways. First, other inhibitors of protein synthesis at the level of transcription, translation and protein assembly may be used. Second, the dosage levels may be different, with daily dosages of doxycycline as low as 1 mg/kg, minocycline as low as 2 mg/kg, and sirolimus as low as 0.5 mg/kg. On the upper end the dosages may be as much as 900 mg/kg (e.g., 450 mg/kg twice per day) of doxycycline, 900 mg/kg (e.g., 450 mg/kg twice per day) of minocycline, and 40 mg/kg (e.g., 20 mg/kg twice per day) of sirolimus. The dosages specified above are for a fully-grown adult cow. Dosage may be correlated to body weight, with heavier animals receiving a larger dose and lighter animals receiving a smaller dose. Dosages need not be correlated to age, weight, breed, and type of animal. In certain instances, rather than administer 900 mg/kg or 400 mg/kg, only 900 mg or 400 mg need be administered to the animal. Dosages may be slow release. In other instances, a dosage of 10 mg/kg tetracycline for Pig, Cattle, Dogs, Cats, and other mammals may be appropriate.

How often the treatment in pill, tablet, or capsule form is taken may be varied, as may the time of day. Every other day may be sufficient for some animals, or three days on and two days off. These are examples of drug holidays. Dosage may be different day-to-day. Time of day for taking the medication may be selected based upon the animal having an empty stomach for better absorption. Dosage when mixed with feed or water may be varied based on when the animals finish a meal or feed. For example, if a corn trough is filled with a doxycycline treatment, the next time the trough is filled it may be filled with minocycline treatment.

The drugs may be combined with an animal's food and/or water. An animal may be fed tablets directly, or tablets may be put in a suspension and fed to the animal. Doxycycline hyclate may be used. An oral suspension such as minocycline hydrochloride may be used. The antibiotics may be injected into the animal directly. A combination of drug delivery may be favorable (e.g., a pill in the morning, combination with food in the afternoon and an injection at night).

In scenarios when it is impractical to administer specific dosages to an entire herd, treatment of the herd's drinking water or feed lot may be favorable. However, the proper dosage of antibiotic and immunosuppressant is nonetheless desired based off the animals drinking or eating food. Dosage calculations can be directed to the volume of water or amount/weight of food while keeping in mind what animal will be consuming it. For example, to treat swine, a proper tetracycline dosage may be 100 mg/ml doxycycline hyclate per 1,000 liters of drinking water. Smaller animals such as rabbits and dogs may only need 100 mg/ml doxycycline hyclate per 2,000 liters drinking water. For cows a range of 200 g-500 g tetracycline per ton of feed may be appropriate.

Side effects of an overdose of doxycycline and other antibiotics in animals include nausea, vomiting, or difficulty swallowing or breathing. Nausea can be reduced if the antibiotic treatment is given with food or if the animal is fed food shortly after in the event the drug is administered through injection or pill. Swallowing and breathing problems may be remedied by administering water to the animal shortly after the antibiotic is consumed.

The dosage of antibiotics may be less important in non-human mammals than in humans. For example, in cows as long as the sequence of antibiotics taken follows procedure, the animal's caretaker may need only add a plethora of antibiotic to an animal's feed or water to gain needed results.

For animals with a first or second degree relative diagnosed with neurodegenerative disorder and a positive saliva amyloid beta 42 test of 40 pg/ml or greater by ELISA, the same regime prevents neurodegenerative or effectively treats undiagnosed neurodegenerative and may be used as a preventative therapy.

The therapy may be used as a diagnostic tool. Thus, if it is suspected that an animal may be afflicted with a neurodegenerative disorder, the treatment regime may be applied as a relatively low cost, fast and harmless test.

Other antibiotics which may be used that inhibit protein gene transcription, translation and synthesis may be selected as well.

Despite the failure of BACE-1 inhibitors in treating neurodegenerative diseases, the amyloid protein deposition hypothesis is valid. Previous studies failed because the inhibitors acted downstream in the metabolism of amyloid protein. The therapies described herein work at the level of DNA transcription to RNA and RNA transport to the mitochondrion for protein synthesis by binding to the 30S and 50S subunits of the RNA to block amyloid protein synthesis. Furthermore, previous studies did not teach the prolonged usage of antibiotics, as well as the varying of tetracyclines as the treatment progressed. Plus, normal cellular catabolism eliminates already deposited amyloid protein.

The therapies described above are also effective for other prion protein complex infections. These include Creutzfeldt Jakob disease (CJD), Lewy body disease, Parkinson's disease, amyotrophic lateral sclerosis (ALS), cerebral amyloid angiopathy, Down's syndrome, BSE, transmissible mink encephalopathy, chronic wasting disease, feline spongiform encephalopathy, and exotic ungulate encephalopathy.

Closing Comments

Throughout this description, the embodiments and examples shown should be considered as exemplars, rather than limitations on the apparatus and procedures disclosed or claimed. Although many of the examples presented herein involve specific combinations of method acts or system elements, it should be understood that those acts and those elements may be combined in other ways to accomplish the same objectives. With regard to flowcharts, additional and fewer steps may be taken, and the steps as shown may be combined or further refined to achieve the methods described herein. Acts, elements and features discussed only in connection with one embodiment are not intended to be excluded from a similar role in other embodiments.

As used herein, "plurality" means two or more. As used herein, a "set" of items may include one or more of such items. As used herein, whether in the written description or the claims, the terms "comprising", "including", "carrying", "having", "containing", "involving", and the like are to be understood to be open-ended, i.e., to mean including but not limited to. Only the transitional phrases "consisting of" and "consisting essentially of", respectively, are closed or semi-closed transitional phrases with respect to claims. Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. As used herein, "and/or" means that the listed items are alternatives, but the alternatives also include any combination of the listed items.

It is claimed:

1. A method of reducing amyloid beta protein and PrPsc fusion protein complex in an animal in need thereof comprising administering to the animal an effective amount of an antibiotic, wherein the antibiotic comprises a tetracycline, wherein the antibiotic interrupts transcription of a gene for amyloid precursor protein and PrPsc fusion protein complex and the RNA transcript at the level of DNA transcription to RNA, RNA transport to the mitochondrion for protein synthesis and deposition in the cerebral cortex neurons;

wherein the animal is a mammal and administered at least 1 tetracycline in a dosage of at least 1 mg, which at a once daily-dosage will give steady state blood levels of tetracycline of a minimum of 0.01 μg/ml and a maximum of 10.0 μg/ml;

wherein the animal is a swine;

wherein the animal has a humoral immune system, wherein the medication includes an immunosuppressant, wherein the immunosuppressant impairs the humoral immune system from synthesizing humoral antibodies, amyloid beta and PrPsc protein.

2. The method of claim 1 wherein the antibiotic is selected from a group consisting of doxycycline or minocycline.

3. The method of claim 1 where the dosage of antibiotic is adjusted at least in part by the weight of the animal.

* * * * *